Figure 1:
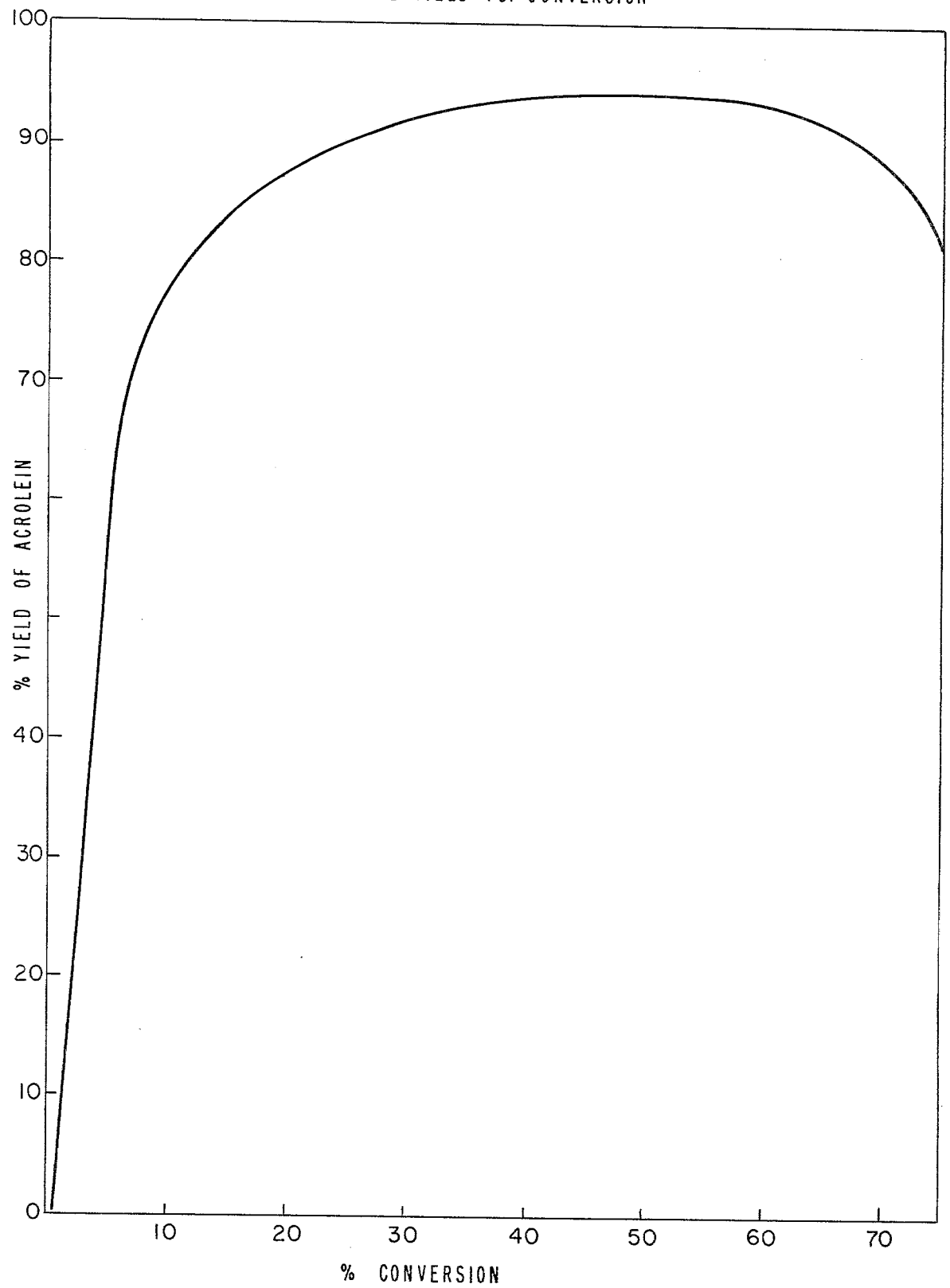

United States Patent [19]

Yates

[11] 4,335,264
[45] Jun. 15, 1982

[54] HIGH YIELD, LOW BYPRODUCT α,β-UNSATURATED ALDEHYDES FROM OLEFINS

[75] Inventor: Paul C. Yates, Wilmington, Del.

[73] Assignee: E. I. Du Pont de Nemours and Company, Wilmington, Del.

[21] Appl. No.: 703,285

[22] Filed: Jul. 7, 1976

[51] Int. Cl.³ ............................................. C07C 45/34
[52] U.S. Cl. .................................. 568/479; 568/476; 568/478; 562/546; 562/547
[58] Field of Search .......... 260/604 R, 526 N, 533 N; 252/437; 568/479, 478, 476; 562/546, 547

[56] References Cited

U.S. PATENT DOCUMENTS

| 3,524,823 | 8/1970 | Eden et al. | 252/437 |
| 3,565,826 | 2/1971 | Sennewald et al. | 252/437 |
| 3,716,496 | 2/1973 | Yoshino et al. | 260/604 R |
| 3,799,978 | 3/1974 | Ohara et al. | 260/533 N |
| 3,804,903 | 4/1974 | Hagiwara | 260/604 R |
| 3,825,502 | 7/1974 | Takenaka et al. | 252/456 |
| 4,001,317 | 1/1977 | Grasselli et al. | 260/533 R |
| 4,035,418 | 7/1977 | Okada et al. | 260/533 R |

Primary Examiner—Werren B. Lone

[57] ABSTRACT

The catalytic vapor phase oxidation of an olefin of 3 to 5 carbon atoms to α,β-unsaturated aldehydes with the formation of substantially no α,β-unsaturated acids is achieved by contacting the olefin, oxygen, an inert gas or moderator and optionally water with a catalyst at a temperature of from 300° C. to 500° C. for a period of time sufficient to achieve from 25 to 80% conversion of said olefin to said aldehyde, separating unreacted olefin and byproduct inert gas from the product stream and recycling the unreacted olefin and byproduct inert gas together with additional olefin and oxygen if required to react with said catalyst.

32 Claims, 3 Drawing Figures

TYPICAL YIELD VS. CONVERSION

TYPICAL YIELD VS. CONVERSION

HIGH YIELD, LOW BYPRODUCT α,β-UNSATURATED ALDEHYDES FROM OLEFINS

BACKGROUND OF THE INVENTION

1. Field of the Invention

This invention relates to a process for the preparation of α,β-unsaturated aldehydes and substantially no α,β-unsaturated acids. More specifically, this invention relates to a process for the preparation of α,β-unsaturated aldehydes and substantially no α,β-unsaturated acids by a vapor phase catalytic oxidation controlled to yield from 20 to 80% conversion of said aldehydes.

2. Prior Art

Numerous catalysts for the vapor phase oxidation of olefins such as propylene, butenes, isobutenes, amylenes, etc., into α,β-unsaturated aldehydes, acids and nitriles have been developed in recent years. These catalysts have broadly included the molybdates, tungstates and vanadates of iron, cobalt, nickel and bismuth. Typical of this art are U.S. Pat. Nos. 3,911,089; 3,855,308; 3,642,930; 3,799,978; 3,825,600; 3,907,712; 3,624,146; 3,959,384 and Canadian Pat. Nos. 930,359 and 982,142.

Characteristic of these patents are the unusual number of elements disclosed to have catalytic activity within the broad spectrum of the compositions. For example, U.S. Pat. No. 3,911,089 discloses no less than 27 elements other than oxygen which may be a portion of, or are required in, the catalyst composition. These include one or more representatives from all of the eight groups of the periodic table and all of the periods of the table from 2 through 6, inclusive. Similarly, U.S. Pat. No. 3,855,308 discloses 19 elements plus 3 more which can be present in the form of substrates for the catalyst to be deposited upon. U.S. Pat. No. 3,642,930 mentions 17 different elements. U.S. Pat. No. 3,799,978 discloses 12 different elements plus a number of others in the form of substrates, as do U.S. Pat. Nos. 3,825,600 and 3,907,712. Not only is the art extraordinarily broad in terms of the possible number of elements which can compose the catalyst and its support, but it is, if anything, even broader in terms of the range of proportions of these elements. For example, U.S. Pat. No. 3,642,930 discloses that the catalyst could be greater than 97% pure bismuth oxide modified with less than 1 atom percent each of iron, molybdenum and an alkali metal or greater than 97% pure iron oxide modified with less than an atom percent bismuth, molybdenum and an alkali metal or greater than 97% pure molybdenum oxide with less than an atom percent of bismuth, iron and an alkali metal or 97% pure cobalt oxide or 97% pure nickel oxide. The catalyst could also encompass the nearly pure phosphates of iron, cobalt, nickel, bismuth or molybdenum as well as the whole range of possible mixed oxides such as iron, cobalt, nickel and bismuth molybdates both as pure compounds and as mixtures in all proportions with one another as well as essentially pure potassium nickel oxides, calcium cobalt oxides, etc. U.S. Pat. No. 3,642,930 is more or less characteristic of the above cited patents in the broad range of compositions to which it is directed.

U.S. Pat. No. 3,624,146 discloses that even minor modifications in the composition of a catalyst can dramatically change its effectiveness. The method of preparation of the catalyst, its temperature of heating, the particular crystalline modification and the structural arrangement of the catalyst have a dramatic impact on its selectivity and activity. Table I of said patent discloses that freshly prepared cobalt molybdate has very poor selectivity toward the desired α,β-unsaturated aldehydes and acids, namely acrolein and acrylic acid, and primarily catalyzes the oxidation of propylene to carbon monoxide, carbon dioxide and acetic acid. Simply by heat-treating this same catalyst at a temperature of 1200° F. the selectivity for acrylic acid is improved by a threefold factor whereas that for acrolein is improved by a dramatic twentyfold factor. By substituting as little as 10 atom percent of the cobalt in the structure with bismuth, an additional threefold improvement is achieved in the case of acrolein and a 50% improvement in the acrylic acid selectivity. If the bismuth concentration is now further increased to a range of 20% of the cobalt concentration, the increase in selectivity toward acrylic acid is dramatically reversed whereas that toward acrolein continues to improve. Specifically, relative to the 10 atom percent bismuth composition, the selectivity toward acrylic acid has been dropped by a fourfold factor, whereas that toward acrolein has been improved by a further factor of two-and-a-halffold.

Thus, it is clear that the extremely wide range in chemical compositions characteristic of this body of art teaches very little in respect to when the literally tens of millions of possible structures and compositions within the scope of each patent should be employed to accomplish any particular reaction with a high selectivity and yield.

U.S. Pat. No. 3,959,384 discloses the propylene oxidation by a process that increases the single pass yield of acrolein. This process, however, like that of the aforesaid references, results in the production of 3 to 10% acrylic acid.

In the preparation of acrolein by the catalytic oxidation of propylene the accompanying formation of acrylic acid with the product poses a serious disposal problem. The acrolein and other desired products may be separated from the product stream which may contain acrolein, acrylic acid, acetic acid, acetaldehyde, other condensable impurities and water by adsorption. Distillation may be used for further separation of e.g., acrolein, but the acid present in the final dilute aqueous acid stream cannot be recovered economically. The aqueous acid stream may be incinerated; however, the very high water content and low fuel content require large amounts of costly fuel. The aqueous acid stream may be treated in an activated sludge type biochemical process. However, the investment in biochemical waste disposal equipment would be extremely high in even a medium size acrolein plant. The loss itself of even a 5% yield to acrylic acid is a matter of no minor consequence in view of the rapidly escalating cost of hydrocarbons.

The art, taken either individually or together fails to show a process for oxidizing propylene wherein there is achieved high yields of α,β-unsaturated aldehydes coupled with very low concentrations of subsequent oxidation products of these aldehydes such as the α,β-unsaturated acids.

SUMMARY OF THE INVENTION

Now it has been found that by control of the chemical composition of the catalyst employed, by simultaneous control of the concentration of moderators which are a portion of the feedstream as well as by a control of the time, temperature and the relative proportions of reactants employed in the feed compositions, an extremely selective oxidation can be made to take place with a minimum formation of the undesirable α,β-unsaturated acids the yields and/or selectivities to α,β-unsaturated aldehydes exceeding 80%, while yields and/or selectivities to α,β-unsaturated acids are below 2% and preferably below 0.5% The process of this invention involves the simultaneous control of all the aforesaid factors within rather precise limits. In the process of the invention the use of the preferred catalysts hereinafter described without appropriate attention to the process variables taught herein will not yield the desired results. Similarly, unless the catalysts of the invention which satisfy a rather complex and narrow set of interrelationships among the catalyst constituents are utilized, it will not be possible to achieve the desired results.

What is meant by yield or selectivity is the moles of α,β-unsaturated aldehyde in the product divided by the difference between the moles of olefin in the feed and the moles of olefin in the product expressed in percentage form.

What is meant by conversion is the moles of olefin in the feed minus the moles of olefin in the product divided by the moles of olefin in the feed expressed in percentage form.

The catalysts of the invention are defined by the general formula:

$$R_a Co_b Fe_c Ni_d Q_e M_f Y_g Z_h O_x$$

where
R = Bi or Sb
Q = Mo, W, V or mixtures thereof
M = P, Si or Te
Y = alkali or alkaline earth metals (Groups Ia and IIa of the periodic table)
Z = Ag or Tl
and a is 0.6 to 6.0 (preferably 0.7 to 5.0, most preferably 0.8 to 3.6); b is 0 to 3.9 (preferably 1.0 to 3.7, most preferably 1.5 to 3.5); c is 0 to 10.2 (preferably 1.0 to 4.0, most preferably 1.5 to 3.5); d is 0 to 10.2 (preferably 0.5 to 8.0, most preferably 1.0 to 7.0); e is 12; f is 0 to 2.0 (preferably 0.05 to 0.40, most preferably 0.06 to 0.35); g is 0 to 2.0 (preferably 0.05 to 0.20, most preferably 0.06 to 0.15); h is 0 to 2.0 and x is as required to satisfy valence of the other elements with the proviso that:
Σb+c+d must be >6 and preferably between 7 and 11, and
Σb+d must be >5.

Thus, the vapor phase selective oxidation process of the invention for the preparation of α,β-unsaturated aldehydes and less than 2% α,β-unsaturated acid (preferably less than 0.5% α,β-unsaturated acid) comprises contacting a reactant gas containing from 1 to 30 volume percent of an olefin of 3 to 5 carbon atoms, from 0 to 40% (preferably 10 to 40%) by volume of H₂O, from 0.25 to 2 times the concentration of olefin of O₂ and from 15 to 97 volume percent (preferably 25 to 88%) of an inert gas or a moderator with a catalyst of the general formula $$R_a Co_b Fe_c Ni_d Q_e M_f Y_g Z_h O_x$$

where R, Q, M, Y, Z and a, b, c, d, e, f, g, h and x are as defined above for a period of time at a temperature and a pressure that will produce a gaseous product stream comprising α,β-unsaturated aldehyde at a conversion of from 25 to 80% based on the olefin, a byproduct inert gas or moderator and a mixture of acids and other aldehydes, separating the byproduct inert gas or moderator from the product stream, contacting the byproduct inert gas or moderator together with additional olefin and oxygen to achieve a composition within that required initially with the catalyst and separating and recovering the α,β-unsaturated aldehyde.

Representative examples of the α,β-unsaturated aldehyde of this invention include acrolein, crotonic aldehyde, methacrolein, pent-2-ene-1-ol, 3-methyl-but-2-ene-1-ol and 2-methyl-but-2-ene-1-ol.

Representative examples of the olefins of this invention include propene-1, 2-methyl butene-1, 2-methyl propene-1, pentene-1, pentene-2, 3-methyl-but-2-ene and 2-methyl-but-2-ene.

Although the formula given above seems exceedingly complex and broad, there is a rational basis for each aspect of the catalysts of the invention. To begin with, molybdenum, tungsten and vanadium are almost unique among all the elements of the periodic table in that they possess the capacity to form polymeric anions composed of octahedra of $MoO_6$, $WO_6$ or $VO_6$ surrounding and sharing oxygens with a central atom. This central atom can be another atom of tungsten, molybdenum or vanadium, in which case the complex anions so formed are known as isopolyanions, or it can be a tetrahedrally arranged or octahedrally arranged foreign central atom such as phosphorus or silicon (which are examples of tetrahedrally oriented central atoms) or tellurium (as an example of an octahedrally oriented central atom). The resulting large, polymeric, three-dimensional anions form rather loosely packed crystal structures with unusually large interstices between the anions capable of accommodating a large number of molecules of water (or even metallic oxides of sufficiently small size such as the oxides of Group Ia in the periodic table along with silver and thallium).

These same polymerized large anions tend to form layer-lattice structures in conjunction with transition metal oxides such as iron, cobalt, nickel, bismuth and antimony. In such layer-lattice structures, layers of the polymerized molybdate, tungstate or vanadate anions are bonded through oxygen to layers of transition metal oxides such as iron, cobalt, nickel, bismuth or antimony. Since the complex anions can accommodate as a central atom either another of their own elements or a foreign element such as phosphorus, silicon or tellurium, and since in any event the central atom in this arrangement is totally surrounded with tungstate, molybdate or vanadate ions, it usually does not cause a great deal of difference in the overall packing and other properties when such substitutions are made. It is for this reason that phosphomolybdates, silicomolybdates and similar tellurium-containing compositions closely resemble the corresponding molybdates, vanadates and tungstates which do not contain the heterocentral atom.

Further, it is a relatively simple matter for the molybdates, tungstates and vanadates as well as their phospho-, silico- and tellurium-containing derivatives to isomorphously substitute for one another, forming a continuous series of solid solutions. Thus, mixtures of these elements with one another possess properties which are comparable to those of the individual oxides.

It is also important to note that bismuth and antimony oxides are strongly basic, particularly bismuth oxide, and possess relatively low surface energies; cobalt, nickel and iron oxides are moderately basic but possess quite high surface energies; and the tungstates, molybdates, vanadates and the heteropoly acid mixed oxides such as the phosphomolybdates are strongly acidic oxides.

In order to achieve an extraordinarily high selectivity toward $\alpha,\beta$-unsaturated aldehydes, it is necessary to do an extremely difficult task. One must first adsorb an olefin, cause it to react with oxygen to form the aldehyde without oxidatively attacking the double bond to form undesired products such as acetaldehyde and acetic acid, and then desorb the $\alpha,\beta$-unsaturated aldehyde before it is further oxidized to the undesired $\alpha,\beta$-acid such as acrylic acid, or to the even more undesired generalized oxidation products such as carbon monoxide, carbon dioxide, formaldehyde, etc. The difficulty of doing this can be judged from the fact that aldehydes in general are rather more easily oxidized than hydrocarbons.

It is believed that the catalysts of this invention function in the following manner: The olefin is thought to adsorb onto a molybdenum, tungsten or vanadium oxide layer by a donation of electrons from the double bond of the olefin to the highly positively charged surface atoms of molybdenum, tungsten or vanadium. This transiently adsorbed molecule then suffers a drift of electrons in the direction of the metal atom, thus activating the hydrogen atoms on the adjacent carbon to the double bond, by depleting this carbon atom of its normal complement of electrons. Adsorbed oxygen molecules or ions (probably chemisorbed onto the surface of more basic metal atoms such as bismuth, iron, cobalt or nickel) in an adjacent layer may then join the electron-depleted carbon atom to form an allyl hydroperoxide which can split out water and form a desired $\alpha,\beta$-unsaturated aldehyde. The reverse electron drift toward the newly added oxygen atom may then deplete the electron concentration at the double bond, weakening its attachment to the underlying molybdenum, tungsten or vanadium atom and allowing it to pull free into the gas phase as a product molecule. The catalysts of this invention require a fairly balanced ratio between the molybdate, tungstate or vanadate acidic layer structure and the more basic oxides such as bismuth, cobalt, iron or nickel. The catalysts of this invention also require the presence of at least small amounts of antimony or bismuth, with bismuth being preferred. This is thought to be connected with the previously noted fact that the surface energy of antimony or bismuth oxides are much lower than the surface energy of the corresponding iron, cobalt or nickel oxides. A very high surface energy oxide will tend to retain a polar molecule on its surface for a much longer period of time than will a low surface energy oxide.

It is not necessary to have a large amount of low surface energy oxide in a mixture with higher surface energy oxides because there will be a strong tendency for the lower surface energy oxide to be enriched in the surface layers of the compositions. This is because of the overall tendency of high surface energy oxides to minimize their surface energies by selectively enhancing the concentration of low energy components at the surface. Thus, even when as little as a few atom percent of an oxide such as bismuth is present mixed with a much larger quantity of high energy oxides such as iron, cobalt or nickel, the surface composition will still be such that relatively large quantities of bismuth may be present in the surface layers.

Excessive quantities of bismuth oxide are not desired since this oxide has a very strong tendency to retain acidic materials because of its highly basic character. Even the $\alpha,\beta$-unsaturated aldehydes can behave as acids toward sufficiently strong bases. A retention of acidic materials is undesirable since they thereby may be further oxidized to other undesired products. A second reason why excessive amounts of bismuth or antimony oxide is not desired is that such oxides have a very strong affinity for absorption of oxygen and on the average a single adsorbed propylene molecule in a high bismuth-containing structure may be surrounded by an excessive number of adsorbed oxygen molecules or ions. This statistically increases the chances of its being oxidized beyond the first stage to form the undesired $\alpha,\beta$-unsaturated acids.

Because of the high activity of cobalt oxide as a generalized oxidizing agent, it will be noted that the amount of this is restricted to where it cannot achieve as much as 4 atoms of cobalt per 12 atoms of molybdenum. Since iron oxide, however, is somewhat too low in oxidative activity, there is also a requirement that the sum of the cobalt and nickel oxides must be greater than 5 to 12 molybdenum, tungsten or vanadium atoms.

The process of this invention provides a high selectively to $\alpha,\beta$-unsaturated aldehydes and simultaneously avoids making the $\alpha,\beta$-unsaturated acids. If one is making acrolein, for example, the usual commercial procedure for recovery involves absorbing the acrolein, acrylic acid, acetic acid, acetaldehyde and other condensable impurities in water after the propylene-oxygen-inert gas feed mixture has been contacted with the heated catalyst. The $\alpha,\beta$-unsaturated aldehyde, such as acrolein, is then separated by distillation from the low-boiling impurities such as formaldehyde, acetaldehyde, and from the less volatile impurities such as acetic acid and acrylic acid which remain in the aqueous adsorbent stream. The resulting stream of dilute aqueous acid represents a serious problem in disposal.

The processes of this invention greatly minimize the expense and potential pollution threat to the environment of the relatively high byproduct acid content of the synthesis streams. This is achieved by a close control of the variables of catalyst composition, catalyst contact time, temperature, pressure, relative proportions of the olefin and oxygen in the gas feeds, by the addition of moderators, by control of the surface area of the catalyst and by close control over the degree of conversion achieved per pass.

In the processes of the invention, temperatures in the catalyst bed can range from approximately 300° C. to 500° C. It is preferred to operate in the range of 300° C. to 400° C. and most preferred to operate in the range from 310° C. to 380° C. The gases can be preheated before contacting the catalyst to temperatures between 100° C. and 200° C. This preheating shortens the contact time and permits higher flow rates.

The overall pressure of the reaction is not highly critical and can range from atmospheric pressure to as much as 10 atm. Since for the primary reactions of invention the number of moles of products is the same as the number of moles of reactants, the reaction is not strongly influenced by pressure. The most preferred operating range is from about 1 to 4 atm with 1.5 to 3.5 atm most highly preferred.

In general, most of the conventional procedures for contacting a gas stream with a solid heterogeneous catalyst can be employed in the processes of the invention. Thus, one may employ fluidized bed techniques, so-called ebullient or boiling bed techniques, fixed bed techniques such as plug flow reactors, and fast fluidized bed or entrained catalyst techniques in which the catalyst is circulated in the flowing gas stream and subsequently recovered and separated from the products and recycled.

The preferred catalyst contact times are dependent upon the chemical activity of the catalyst, which, in turn, depends on its composition and surface area, as well as the technique used to contact the catalyst with the reactants. It also depends on the temperature of the reaction and the concentration levels of reactants in the feed streams. Because these can vary over quite a broad range and because these variables interact with one another to a substantial degree, it is not possible to give arbitrary preselected contact times. Broadly the contact times should range from about 0.1 second to 10 seconds with the range of 0.3 to 5 seconds preferred, and the range from about 0.5 to 4 seconds highly preferred. The contact time will vary inversely with the temperature chosen. In general, it is desirable to have short contact times when operating in the upper temperature range disclosed. Similarly, it is desired to have longer contact times when operating at temperatures in the lower end of the range.

The inert gas or moderator of this invention, in contrast to the byproduct inert gas or moderator comprises one or more gases selected from the group consisting of nitrogen, carbon monoxide, carbon dioxide and hydrogen. Other gases within the scope of the inert gas or moderator of this invention include helium, argon, neon, etc. which, however, are more expensive and possess no specific advantage. The preferred inert gas or moderator of this invention is one or more gas selected from the group consisting of carbon dioxide, carbon monoxide and hydrogen. The most preferred inert gas or moderator is one or more gas selected from the group consisting of carbon dioxide and carbon monoxide. It is understood that the feed stream of this invention comprises, in addition to the olefin, impurities normally present with the olefin. Generally these impurities are ethane, methane, propane or butane.

The most preferred inert gas in the process of the invention is carbon dioxide. Mixtures of carbon dioxide with carbon monoxide are also highly preferred inerting mixtures. Mixtures of these two gases which also may contain the impurities of the starting olefin, e.g., propane in propylene, are still useful inerting gases. Carbon monoxide and carbon dioxide are most preferred since carbon monoxide and carbon dioxide are the principal byproducts of the reaction when operating in the preferred conversion range of the processes of this invention. However, in order to achieve the desired reactant feed composition, small amounts of carbon dioxide and carbon monoxide formed in each pass through the reactor may have to be removed by a purge of a quantity of the total byproduct inert gas or moderator mixture made per pass, following condensation and absorption of the $\alpha,\beta$-unsaturated aldehyde and other water soluble impurities.

Nitrogen, while it is within the scope of the inert gas or moderator of the invention, has the disadvantage that specialized absorption procedures have to be employed to adjust the byproduct inert gas or moderator gas mixture composition. Merely venting will not yield the desired composition. Procedures known in the art may, however, be utilized such as absorption in basic solutions including amines, sodium carbonate, sodium arsenate, etc., but this does add to the complexity and to the investment of the processes of the invention.

The byproduct inert gas or moderator produced in the process of the invention is accompanied by the desired $\alpha,\beta$-unsaturated aldehyde and other aldehydes with substantially no $\alpha,\beta$-unsaturated acids. The composition of the byproduct inert gas or moderator may vary somewhat depending, among other things, on the purity of the starting olefin. Impurities present in the starting olefin may include $C_1$ to $C_4$ saturated hydrocarbons. In such cases the byproduct inert gas or moderator will include one or more $C_1$ to $C_4$ saturated hydrocarbon permanent gas. Thus, the byproduct inert gas or moderator depending on the inert gas composition of the reactant gas may contain varying amounts of gas mixtures selected from oxygen, carbon monoxide, carbon dioxide, water, hydrogen, nitrogen and unreacted olefin in addition to the saturated hydrocarbon impurity that may be present in the olefin. Most often the $C_1$ to $C_4$ saturated hydrocarbon permanent gas present is one selected from ethane, methane, propane and butane. The $C_1$ to $C_4$ gas is usually propane when the preferred propylene is the olefin.

Thus, the most preferable inert gas or moderator feed of this invention comprises one or more gases selected from carbon dioxide, carbon monoxide, hydrogen and the $C_1$ to $C_4$ saturated permanent gas impurity present in the olefin while the byproduct inert gas or moderator comprises mixtures of gases selected from the group consisting of oxygen, carbon monoxide, carbon dioxide, water, hydrogen and unreacted olefin with a $C_1$ to $C_4$ saturated hydrocarbon impurity.

The amount of the olefins of the invention can range from about 1% by volume to 30% by volume in the feed stream with the range from 1% to 15% preferred and from about 5% to 12% being highly preferred. Lower concentrations of olefin lead to an undesirable low degree of product formation per pass and require unreasonably large equipment. Higher concentrations of olefins can create explosion hazards since they may represent operation within the explosive range. Concentrations of oxygen can range from about 0.25 to 2 times the concentration of olefin within the range of 2% to 15% by volume. Preferably they will range from about 1 to 1.5 times, and more preferably from about 1 to 1.3 times the concentration of olefin within said oxygen range of from 2% by volume to 15% by volume. Thus, it is possible to operate with concentrations of oxygen which are less than the concentration of olefin, but when this is done, it is absolutely necessary to adjust the degrees of conversion to insure the maintenance in the exit gas stream of at least 1% by volume of oxygen. This is because the catalysts of the invention require an overall oxidizing atmosphere for their continued successful operation. Thus, when operating at oxygen to olefin ratios of less than 1, it will be necessary to maintain at least 1% by volume of oxygen in the exit gases by control of temperature, contact time, catalyst activity, etc. If this is done, it is possible to operate at oxygen to olefin ratios as low as 0.25:1.

Two of the inert gases or moderators mentioned above, namely steam and carbon dioxide, influence the activity and to some extent the selectivity of the catalyst. That is, in addition to their role as inert gases in controlling flammability and explosive limits, they are apparently in some manner adsorbed onto the catalyst surface at least in a transient manner and thus moderate the activity of the catalyst. Water vapor shows this effect to a greater degree than $CO_2$ and seems to function synergistically with $CO_2$. For this reason, it is preferred to include minor amounts within the range of 10% to 40% by volume of the feed stream as water vapor. In the presence of high concentration of $CO_2$, the amount of water required is substantially less than that needed if $CO_2$ is not present, to achieve the same degree of moderation of the catalyst activity. It is for this reason that $CO_2$ is singularly the most preferred inert gas or moderator in the processes of this invention. When operating with the order of 50% $CO_2$ in the system, the amounts of water needed to moderate the catalyst activity can be as little as half of the 30% or more which is classically employed in prior art processes. Thus, $CO_2$ and water are the most preferred combinations of this invention.

One of the most critical properties of the processes of this invention is the control of the degree of conversion. The maximization of the production of acrolein and other $\alpha,\beta$-unsaturated aldehydes by operating at very high conversions such as 90% or greater is definitely not desired in the process of this invention. FIG. 1 is a graph showing a typical yield vs. percent conversion figure for the conversion of propylene to acrolein typically achieved under the conditions of this invention.

Referring now to FIG. 1, it will be noted that below conversions of 20%, yields are very poor and also again above 75 to 80% conversions yields would be relatively poor.

Figure 2:
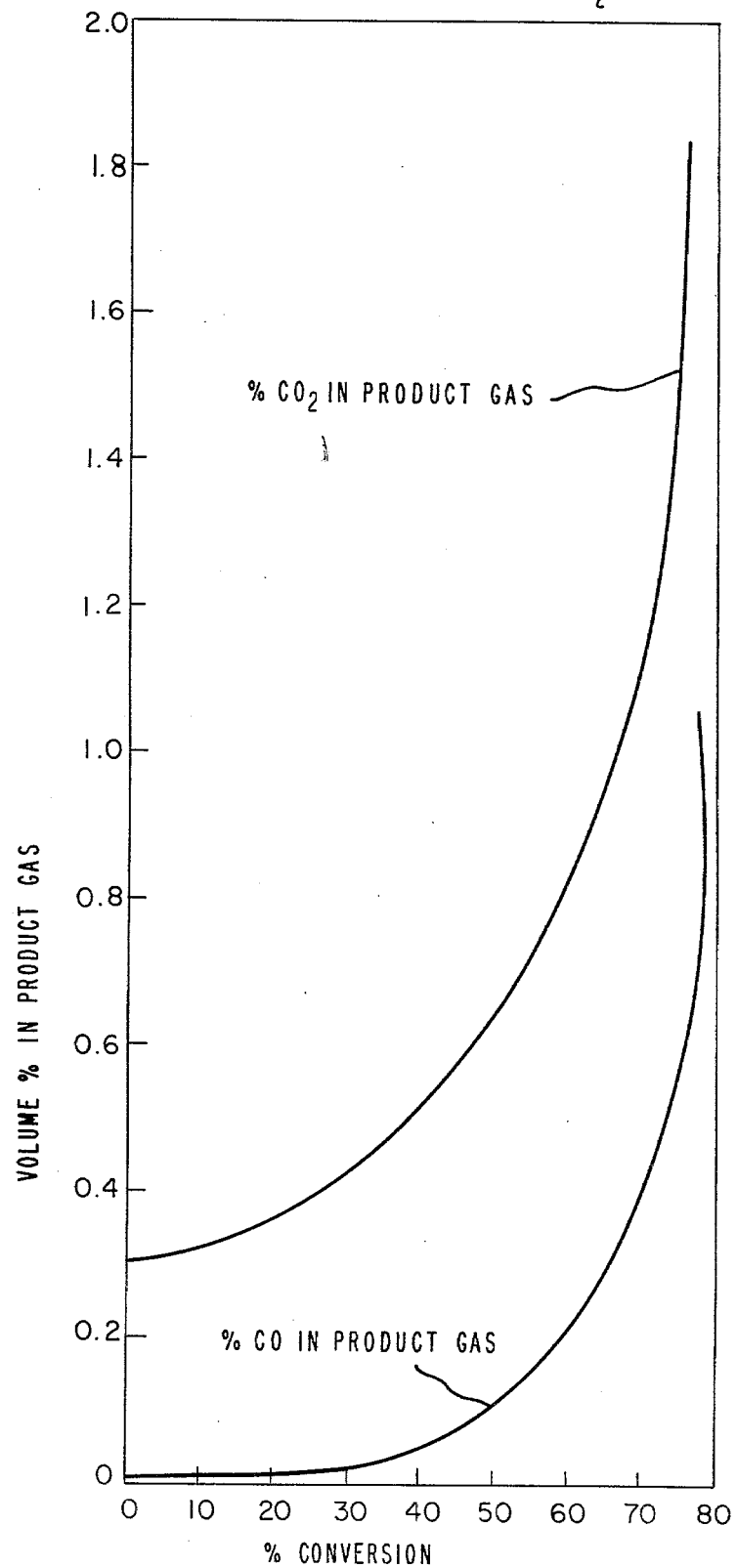

FIG. 2 is a graph generally showing the increase in the CO and $CO_2$ has typically resulting when the conversion of propylene to acrolein is increased. Referring now to FIG. 2, the rapid formation of undesired carbon monoxide and carbon dioxide in the range of 60% conversion and greater are typically illustrated as the conversion increases. Thus, conversions above 80% are to be avoided.

Figure 3:
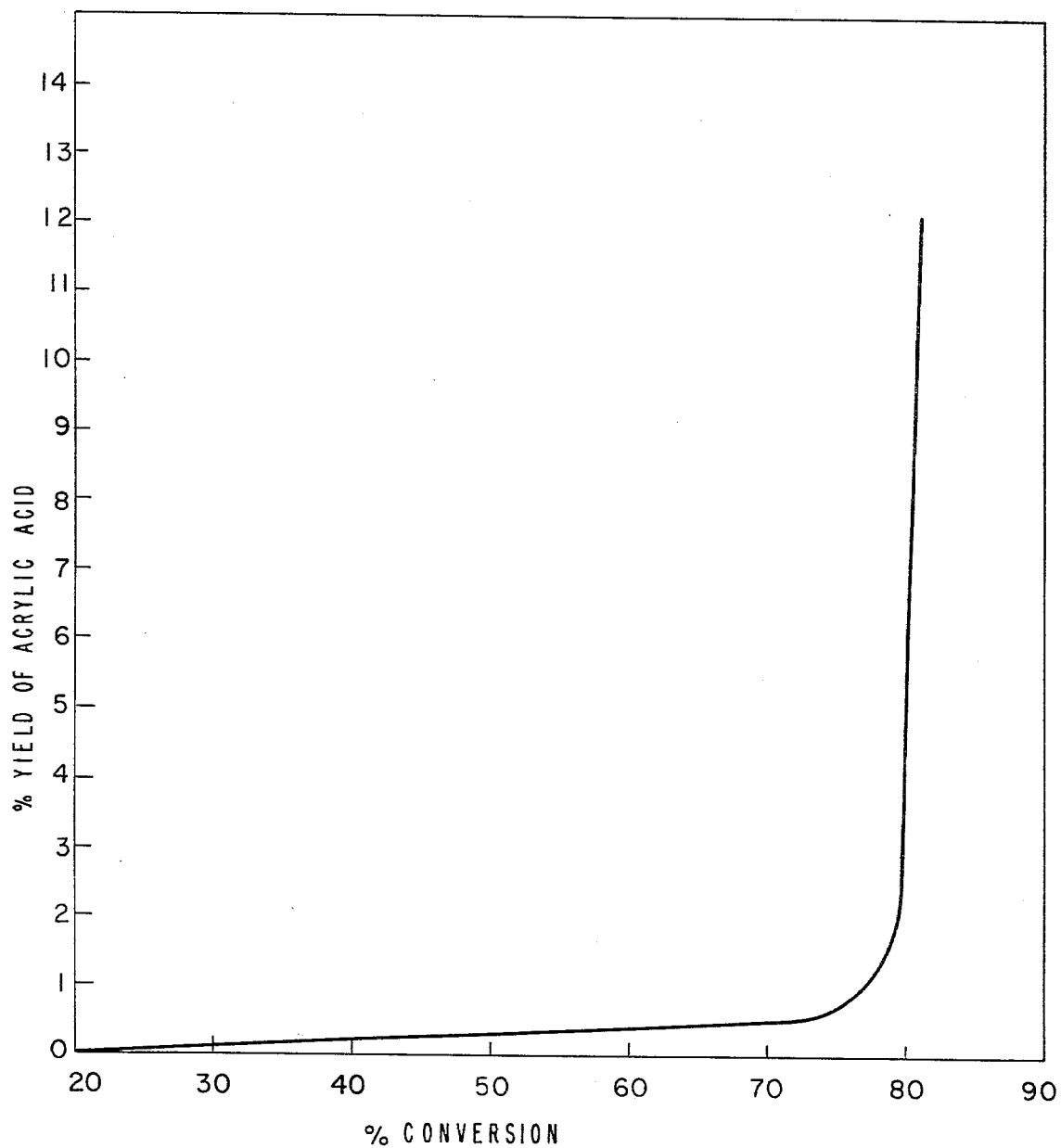

FIG. 3 is a graph which shows the formation of the undesired acrylic acid byproduct with increased conversion. Referring now to FIG. 3, the graph shows the rapid increase of acrylic acid after about 80% conversion of propylene to acrolein. Thus, conversions above 80% are to be avoided. FIGS. 1, 2 and 3 are typical of findings within the scope of the present invention and do not necessarily represent any one run set of conditions.

Table I summarizes a very large number of prior art examples gathered from the patent literature which show operations at conversions below 80%. It will be seen that the formation of acrylic acid byproduct is not suppressed simply by operating at lower conversions when using the catalysts of the prior art. Therefore, operation at low conversion without anything more will not achieve the benefits of the present invention. The process of the present invention requires the catalyst described herein.

In the processes of this invention, it is generally desired to operate at conversions between 25% and 80%. It is more preferred to operate at conversions ranging from 35% to 75%, and it is most highly preferred to operate in the range of 40% to 70% conversions. It is a relatively simple matter to ascertain the appropriate degree of conversion for any preselected feed composition, catalyst, temperature, etc., within the general range of conditions previously discussed.

The processes of the invention encompass a recycling of the unconverted propylene and oxygen as well as the byproduct inert gas or moderator or mixture of gases following the separation of the oxygenated products of the invention from the product stream. While the conversion under this invention is controlled between 25% to 80%, the cummulative conversions finally achieved by the process of this invention, considering the unreacted propylene that is recycled, generally are as high as 97%. However, the formation of $\alpha,\beta$-unsaturated acids remains substantially zero even after the recycling step in the process of the invention.

In the process of the invention the unreacted olefin and oxygen within the byproduct inert gas or moderator mixture are recycled to achieve a satisfactory conversion of substantially all the olefin to the desired end product. This can be accomplished by absorbing from the product stream, e.g., the acrolein, methacrolein or other $\alpha,\beta$-unsaturated aldehyde into an aqueous solution along with water-soluble byproducts including formaldehyde, acetaldehyde, acetone, acrylic acid, acetic acid and the like. These may be purified by distillation as previously noted. The $\alpha,\beta$-unsaturated aldehyde, e.g., acrolein not absorber by the aqueous stream is removed by passing the product stream through an absorber that will remove essentially all of the aldehyde, e.g., acrolein not adsorbed by the aqueous stream. After absorption, the stream will consist of unconverted olefin, unreacted oxygen, impurities in the olefin and the inert gas or moderator employed. This is supplemented as necessary with additional olefin and oxygen and recycled back over the catalyst to prepare additional quantities of $\alpha,\beta$-unsaturated aldehydes, e.g., acrolein.

To illustrate the suprising selectivity of the catalyst of the present invention various catalyst compositions of the prior art are summarized in Table I to illustrate the selectivity of prior art catalysts.

TABLE I

| | SELECTIVITY OF PRIOR ART PROCESSES | | | | | | | | | | | | | | |
|---|---|---|---|---|---|---|---|---|---|---|---|---|---|---|---|
| | Composition of Catalyst (Atomic Ratio) | | | | | | | | | | | % | % $\alpha,\beta$- | % $\alpha,\beta$- | |
| Patent | Co | Fe | Bi | W | Mo | Si | Tl | K | Ag | P | Mg | As | Conversion | Aldehyde | Acid | Temperature |
| Can. 980,359 | — | 5.0 | 1.3 | — | 12 | — | — | 0.2 | 0.1 | 0.1 | — | — | 47.2 | 84.3 | 6.3 | 402° C. |
| | — | 5.0 | 1.3 | — | 12 | — | — | — | 0.1 | 0.1 | — | — | 44.5 | 72.2 | 6.1 | 401° C. |
| | — | 0.5 | 1.3 | — | 12 | — | — | 0.2 | 0.1 | 0.1 | — | — | 53.2 | 89.0 | 5.1 | 400° C. |
| | — | 0.5 | 1.3 | — | 12 | — | — | — | 0.1 | 0.1 | — | — | 52.8 | 80.5 | 5.8 | 401° C. |
| | — | 5.0 | 1.3 | — | 12 | — | — | 0.2 | 0.1 | 0.1 | — | — | 43.1 | 90.0 | 4.8 | 375° C. |
| | — | 5.0 | 1.3 | — | 12 | — | — | 0.2 | 0.1 | 0.1 | — | — | 55.7 | 88.6 | 5.7 | 412° C. |
| | — | 5.0 | 1.3 | — | 12 | — | — | 0.2 | 0.1 | 0.1 | — | — | 59.3 | 87.6 | 5.9 | 440° C. |
| | — | 5.0 | 1.3 | — | 12 | — | — | — | 0.1 | 0.1 | — | — | 45.2 | 82.1 | 6.5 | 372° C. |
| | — | 5.0 | 1.3 | — | 12 | — | — | — | 0.1 | 0.1 | — | — | 58.5 | 76.3 | 7.1 | 439° C. |
| | — | 5.0 | 1.3 | — | 12 | — | — | — | 0.1 | 0.1 | — | — | 53.8 | 78.6 | 6.6 | 414° C. |
| | — | 5.0 | 1.3 | — | 12 | — | — | 0.2 | 0.1 | — | — | — | 52.0 | 91.0 | 3.5 | 376° C. |
| Can. 982,142 | — | — | 9.0 | — | 12 | ? | — | — | — | 1.0 | — | — | 22.8 | 2.9 | | 680° F. |
| | — | — | 9.0 | — | 12 | ? | — | — | — | 1.0 | — | — | — | 35.6 | 3.5 | 680° F. |
| | — | 3.0 | 1.0 | — | 12 | ? | — | — | — | 0.5 | 6.5 | — | — | 22.0 | 3.9 | 605° F. |

TABLE I-continued

SELECTIVITY OF PRIOR ART PROCESSES

| Patent | Co | Fe | Bi | W | Mo | Si | Tl | K | Ag | P | Mg | As | % Conversion | % α,β-Aldehyde | % α,β-Acid | Temperature |
|---|---|---|---|---|---|---|---|---|---|---|---|---|---|---|---|---|
| | — | 3.0 | 1.0 | — | 12 | ? | — | — | — | 0.5 | 6.5 | — | — | 48.5 | 6.8 | 680° F. |
| | — | 3.0 | 2.0 | — | 12 | — | — | — | — | 0.5 | 4.5 | — | — | 64.4 | 10.6 | 680° F. |
| | — | 4.0 | 2.0 | — | 12 | ? | — | — | — | — | 4.5 | — | — | 78.3 | 5.7 | 680° F. |
| | — | 4.0 | 2.0 | — | 12 | ? | — | — | — | — | 4.5 | — | — | 54.3 | 17.2 | 680° F. |
| | — | 4.0 | 2.0 | — | — | ? | — | — | — | 0.5 | 4.5 | — | — | 51.2 | 20.6 | 680° F. |
| | — | 4.0 | 2.0 | — | — | ? | — | — | — | 0.5 | 4.5 | — | — | 64.2 | 8.6 | 605° F. |
| | — | 4.0 | 2.0 | — | 12 | ? | — | 0.07 | — | 0.5 | 4.5 | — | — | 71.7 | 12.1 | 680° F. |
| | — | 4.0 | 2.0 | — | 12 | ? | — | — | — | — | 4.5 | 0.5 | — | 68.3 | 10.2 | 680° F. |
| | — | 4.0 | 2.0 | — | 12 | ? | — | — | — | — | 4.5 | — | — | 65.9 | 5.3 | 680° F. |
| U.S. Pat. No. 3,624,146 | 1.0 | — | — | — | 1.0 | — | — | — | — | — | — | — | 27 | 0.3 | 9.7 | 860° F. |
| | 1.0 | — | — | — | 1.0 | — | — | — | — | — | — | — | 29 | 6.5 | 34.4 | 863° F. |
| | 4.0 | — | 1.0 | — | 1.0 | — | — | — | — | — | — | — | 26 | 51.5 | 16.8 | 870° F. |
| | 9.0 | — | 1.0 | — | 1.0 | — | — | — | — | — | — | — | 35 | 20.2 | 48.4 | 798° F. |
| U.S. Pat. No. 3,855,308 | 4.0 | 1.0 | 1.0 | 2.0 | 10 | 1.35 | 0.05 | — | — | — | — | — | 97.5 | 91.5 | 6.0 | 300° C. |
| | 4.0 | 1.0 | 1.0 | 2.0 | 10 | — | 0.05 | — | — | — | — | — | 84.0 | 93.0 | 2.5 | 300° C. |
| | 4.0 | 1.0 | 1.0 | 2.0 | 10 | 1.35 | — | — | — | — | — | — | 81.0 | 77.0 | 6.6 | 300° C. |
| | 4.0 | 1.0 | 1.0 | 2.0 | 10 | 1.35 | 0.08 | — | — | — | — | — | 96.5 | 92.1 | 5.0 | 300° C. |
| | 4.0 | 1.0 | 1.0 | 3.0 | 9.0 | 2.0 | 0.10 | — | — | — | — | — | 97.0 | 91.5 | 5.7 | 295° C. |
| | 5.0 | 1.0 | 2.0 | 1.0 | 11 | 1.1 | 0.05 | — | — | — | — | — | 98.2 | 87.0 | 7.5 | 310° C. |
| | 4.0 | 0.5 | 1.0 | 1.0 | 11 | 1.5 | 0.05 | — | — | — | — | — | 97.5 | 90.8 | 6.8 | 290° C. |
| | 4.0 | 2.0 | 1.0 | 2.0 | 10 | 1.0 | 0.05 | — | — | — | — | — | 98.0 | 88.0 | 7.1 | 320° C. |
| | 4.0 | 1.0 | 1.0 | 2.0 | 10 | 1.35 | 0.03 | Na 0.05 | — | — | — | — | 97.5 | 86.5 | 8.0 | 305° C. |
| | 4.0 | 1.0 | 1.0 | 2.0 | 10 | 1.35 | 0.03 | 0.03 | — | — | — | — | 97.0 | 88.0 | 6.2 | 315° C. |
| | 4.0 | 1.0 | 1.0 | 2.0 | 10 | 1.35 | 0.03 | — | — | — | 0.03 | — | 97.2 | 86.8 | 7.5 | 300° C. |
| | 4.0 | 1.0 | 1.0 | 2.0 | 10 | 1.35 | 0.03 | — | — | — | Ca 0.05 | — | 96.5 | 87.0 | 6.8 | 305° C. |
| | 4.0 | 1.0 | 1.0 | 2.0 | 10 | 1.35 | 0.03 | Na 0.03 | — | — | Ca 0.03 | — | 98.2 | 85.9 | 8.2 | 300° C. |
| | 4.0 | 1.0 | 1.0 | 2.0 | 10 | 1.35 | 0.03 | 0.02 | — | — | 0.05 | — | 97.5 | 87.5 | 7.6 | 310° C. |
| U.S. Pat. No. 3,825,600 | 4.0 | 1.0 | 1.0 | 2.0 | 10 | 1.35 | — | 0.06 | — | — | — | — | 97.0 | 93.0 | 6.1 | 320° C. |
| | 4.0 | 1.0 | 1.0 | 2.0 | 10 | — | — | 0.06 | — | — | — | — | 86.4 | 92.5 | 4.7 | 320° C. |
| | 4.0 | 1.0 | 1.0 | 2.0 | 10 | 1.35 | — | — | — | — | — | — | 94.5 | 71.5 | 11.4 | 320° C. |
| | 3.0 | 1.0 | 1.0 | 2.0 | 10 | 1.35 | — | 0.02 | — | — | — | — | 95.0 | 90.6 | 7.1 | 340° C. |
| | 6.0 | 1.0 | 1.0 | 2.0 | 10 | 1.35 | — | 0.08 | — | — | — | — | 96.8 | 90.2 | 5.3 | 320° C. |
| | 4.0 | 0.5 | 1.0 | 2.0 | 10 | 1.5 | — | 0.06 | — | — | — | — | 97.8 | 90.7 | 6.9 | 320° C. |
| | 4.0 | 2.0 | 0.5 | 2.0 | 10 | 2.0 | — | 0.06 | — | — | — | — | 94.0 | 90.8 | 6.0 | 320° C. |
| | 4.0 | 1.0 | 1.0 | 4.0 | 8 | 3.0 | — | 0.08 | — | — | — | — | 94.8 | 92.6 | 5.2 | 350° C. |
| | 4.0 | 1.0 | 1.0 | 2.0 | 10 | 1.35 | — | 0.06 | — | — | — | — | 96.5 | 91.7 | 6.6 | 320° C. |
| | 4.0 | 1.0 | 1.0 | 2.0 | 10 | 1.5 | — | 0.08 | — | — | — | — | 96.5 | 92.4 | 5.8 | 330° C. |
| | 4.0 | 1.0 | 1.0 | 2.0 | 10 | 1.35 | — | Na 0.02 | — | — | — | — | 96.2 | 90.5 | 6.9 | 320° C. |
| | 4.0 | 1.0 | 1.0 | 3.0 | 9 | 1.35 | — | Na 0.1 | — | — | — | — | 94.8 | 92.2 | 5.4 | 320° C. |
| | 4.0 | 1.0 | 1.0 | 2.0 | 10 | 1.35 | — | Li 0.02 | — | — | — | — | 95.5 | 90.8 | 6.2 | 340° C. |
| | 4.0 | 1.0 | 1.0 | 2.0 | 10 | 1.35 | — | Ca 0.02 | — | — | — | — | 96.5 | 91.1 | 6.4 | 350° C. |
| | 4.0 | 1.0 | 1.0 | 2.0 | 10 | 1.35 | — | Na 0.06 | — | — | 0.10 | — | 96.4 | 92.0 | 5.1 | 340° C. |
| U.S. Pat. No. 3,799,978 | 4.0 | 1.0 | 1.0 | 2.0 | 10 | 1.35 | — | — | — | — | 0.06 | — | 93.0 | 87.2 | 9.0 | 320° C. |
| | 4.0 | 1.0 | 1.0 | 3.0 | 10 | 1.35 | — | — | — | — | Ca 0.06 | — | 90.5 | 82.0 | 12.1 | 320° C. |
| | 4.0 | 1.0 | 1.0 | 3.0 | 9 | 1.5 | — | — | — | — | Ca 0.08 | — | 97.0 | 83.1 | 12.3 | 315° C. |
| | 4.0 | 1.0 | 1.0 | 2.0 | 10 | 1.35 | — | — | — | — | Sr 0.06 | — | 98.5 | 81.0 | 11.4 | 315° C. |
| | 4.0 | 1.0 | 1.0 | 2.0 | 10 | 1.35 | — | — | — | — | — | — | 99.0 | 81.5 | 10.8 | 315° C. |
| | 4.0 | 1.0 | 1.0 | 2.0 | 10 | 1.35 | — | — | — | — | — | — | 94.5 | 71.5 | 11.4 | 320° C. |
| U.S. Pat. No. 3,907,712 | 4.0 | 1.0 | 1.0 | 2.0 | 10 | 1.35 | — | 0.06 | — | — | — | — | 97.0 | 93.0 | 6.1 | 320° C. |
| | 4.0 | 1.0 | 1.0 | 2.0 | 10 | — | — | 0.06 | — | — | — | — | 86.4 | 92.5 | 4.7 | 320° C. |
| | 4.0 | 1.0 | 1.0 | 2.0 | 10 | 1.35 | — | — | — | — | — | — | 94.5 | 71.5 | 11.4 | 320° C. |
| | 5.0 | 0.2 | 1.75 | 1.0 | 11 | 1.35 | — | 0.06 | — | — | — | — | 97.5 | 91.0 | 7.0 | 320° C. |
| | 8.0 | 1.5 | 1.5 | 2.0 | 10 | 0.8 | — | 0.08 | — | — | — | — | 98.0 | 90.0 | 6.8 | 320° C. |
| | 4.0 | 3.0 | 0.4 | 1.5 | 10.5 | 1.35 | — | 0.06 | — | — | — | — | 96.0 | 90.2 | 5.8 | 330° C. |
| | 6.0 | 0.5 | 3.0 | 2.0 | 10 | 3.5 | — | 0.06 | — | — | — | — | 97.0 | 91.5 | 5.4 | 340° C. |
| | 4.0 | 1.0 | 1.0 | 0.5 | 11.5 | 5.2 | — | 0.08 | — | — | — | — | 96.8 | 90.5 | 6.0 | 320° C. |
| | 3.0 | 1.0 | 1.0 | 2.0 | 10 | 1.35 | — | 0.02 | — | — | — | — | 95.0 | 90.6 | 7.1 | 340° C. |
| | 6.0 | 1.0 | 1.0 | 2.0 | 10 | 1.35 | — | 0.08 | — | — | — | — | 96.8 | 90.2 | 5.3 | 320° C. |
| | 4.0 | 0.5 | 1.0 | 2.0 | 10 | 1.5 | — | 0.06 | — | — | — | — | 97.0 | 90.7 | 6.9 | 320° C. |
| | 4.0 | 2.0 | 0.5 | 2.0 | 10 | 2.0 | — | 0.06 | — | — | — | — | 94.0 | 90.8 | 6.0 | 320° C. |
| | 4.0 | 1.0 | 1.0 | 4.0 | 8 | 3.0 | — | 0.08 | — | — | — | — | 94.8 | 92.6 | 5.2 | 350° C. |
| | 4.0 | 1.0 | 1.0 | 2.0 | 10 | 1.35 | — | 0.06 | — | — | — | — | 96.8 | 91.7 | 6.6 | 320° C. |
| | 4.0 | 1.0 | 1.0 | 2.0 | 10 | 1.5 | — | Na 0.08 | — | — | — | — | 96.5 | 92.4 | 5.8 | 330° C. |

TABLE I-continued
SELECTIVITY OF PRIOR ART PROCESSES

| Patent | Composition of Catalyst (Atomic Ratio) | | | | | | | | | | | % Conversion | % α,β-Aldehyde | % α,β-Acid | Temperature |
|---|---|---|---|---|---|---|---|---|---|---|---|---|---|---|---|
| | Co | Fe | Bi | W | Mo | Si | Tl | K | Ag | P | Mg | As | | | | |
| | 4.0 | 1.0 | 1.0 | 2.0 | 10 | 1.35 | — | 0.02 Na | — | — | — | — | 96.2 | 90.5 | 6.9 | 320° C. |
| | 4.0 | 1.0 | 1.0 | 3.0 | 9 | 1.35 | — | 0.1 Li | — | — | — | — | 94.8 | 92.2 | 5.4 | 320° C. |
| | 4.0 | 1.0 | 1.0 | 2.0 | 10 | 1.35 | — | 0.02 | — | — | — | — | 95.5 | 90.8 | 6.2 | 340° C. |
| | 4.0 | 1.0 | 1.0 | 2.0 | 10 | 1.35 | — | 0.02 | — | — | — | — | 96.5 | 91.1 | 6.4 | 350° C. |
| | 4.0 | 1.0 | 1.0 | 2.0 | 10 | 1.35 | — | 0.06 | — | — | — | — | 96.4 | 92.0 | 5.1 | 340° C. |

In all the various illustrated catalysts, the lowest selectivity of acrylic acid was 2.5% at a conversion of 84 mol percent propylene. Regardless of the conversion or of the composition of the catalyst, the acrylic acid was generally much greater.

In the following examples which further illustrate the invention, all percentages are by weight unless otherwise indicated.

EXAMPLES 1-8

A sample of catalyst was prepared having the following composition:

$(K_{0.09}Bi_{0.9}Co_{3.3}Fe_{2.69}Ni_{2.0}P_{0.24}Mo_{12}O_{41.33})_{48\%}$ $(SiO_2)_{52\%}$

The catalyst was prepared by mixing ammonium molybdate dissolved in water, potassium nitrate, phosphoric acid, and an amorphous colloidal silica containing 30 weight percent $SiO_2$ and having a surface of 200 sq m/g of silica together in water in the proportions indicated in the formula. The requisite amount of the nitrates of iron, cobalt, nickel, and bismuth (with the bismuth nitrate stabilized by excess nitric acid) were then mixed with the molybdenum phosphate solution and the mixture heated and stirred until gel formation occurred. The gel was then dried at approximately 270° F., and the resulting catalyst was heat-treated at 600° F. for 5 hours and 1020° F. for 20 hours. It was then crushed and sized through an 8-10 Tyler mesh screen. The resulting catalyst had a surface area of 31 sq m/g. The catalyst was loaded into an 80 mm diameter stainless steel tube having a length of 5.5" and plugged at both ends with quartz wool. This was immersed in a sand bath which could be heated at any desired temperature between 100° C. and 600° C. Cylinders of propylene, oxygen, nitrogen, carbon dioxide were used to feed the desired gas mixtures through rotameters and flow controllers to a mixing zone and from there to a preheater into the catalyst tube immersed in the sand bath. A syringe pump feeding to a vaporizer supplied steam in those reactions where steam was employed. The gas mixture, after passing over the catalyst, was separated into one stream which led to an aqueous absorber and a small sidestream which was taken to a gas chromatographic analytical instrument. The analysis could be performed for oxygen, nitrogen, CO, $CO_2$, water, formaldehyde, propylene or other olefins, acetaldehyde, acrolein, acetic acid, and acrylic acid. When desired, samples from the aqueous absorber could also be recovered and analyzed by wet chemical or other methods. Table II summarizes the data obtained and gives the composition of the gas phase entering the reactor, the yields of acrolein and acrylic acid, and the percent conversion of propylene as well as the temperature and contact time. The concentration of acrylic acid is below detectable limits of the analytical system; namely, less than 0.05% in the gas phase in many of the runs. This contrasts strikingly with that achievable by the known techniques summarized above wherein the acrylic acid is much greater.

TABLE II
EXAMPLES OF THE INVENTION

| Example No. | Feed Compositions in Vol. % | Temp. | Contact Time in Seconds | % Conversion | Acrolein Yield | Acrylic Acid Yield |
|---|---|---|---|---|---|---|
| 1 | 8.51 $C_3H_6$<br>13.51 $O_2$<br>24.09 $H_2O$<br>53.97 $N_2$ | 350° C. | 1.40 | 55.92 | 92.23 | N.D.* |
| 2 | 9.39 $C_3H_6$<br>12.75 $O_2$<br>77.45 $N_2$ | 350° C. | 1.40 | 62.51 | 88.76 | N.D.* |
| 3 | 7.84 $C_3H_6$<br>10.76 $O_2$<br>9.03 $H_2O$<br>72.00 $CO_2$ | 355° C. | 1.40 | 79.41 | 80.00 | N.D.* |
| 4 | 8.79 $C_3H_6$<br>14.99 $O_2$<br>21.36 $H_2O$<br>54.86 $N_2$ | 402° C. | 0.79 | 66.09 | 86.40 | N.D.* |
| 5 | 9.01 $C_3H_6$<br>14.64 $O_2$<br>26.96 $H_2O$<br>49.39 $N_2$ | 455° C. | 0.35 | 34.20 | 92.31 | N.D.* |
| 6 | 9.90 $C_3H_6$<br>12.62 $O_2$<br>16.82 $H_2O$<br>60.65 $CO_2$ | 325° C. | 3.33 | 25.30 | 89.20 | N.D.* |
| 7 | 9.26 $C_3H_6$<br>10.62 $O_2$<br>80.12 $CO_2$ | 350° C. | 1.40 | 66.67 | 87.42 | N.D.* |
| 8 | 8.08 $C_3H_6$<br>11.13 $O_2$<br>80.58 $CO_2$ | 350° C. | 1.40 | 79.31 | 85.50 | .03% |

*N.D. = not detected

EXAMPLES 9-13

The procedure of Examples 1 to 8 was followed with the same catalysts, catalyst bed, and experimental setup except that the feed stream used as the calculated equilibrium feed stream from multiple recycles. Table III summarizes the results.

TABLE III
RECYCLE EXAMPLES OF THE INVENTION

| Example No. | Feed Compositions in Vol. % | Temp. | Contact Time in Seconds | % Conversion | Acrolein Yield | Acrylic Acid Yield |
|---|---|---|---|---|---|---|
| 9 | 12.09 $C_3H_6$<br>11.13 $C_3H_8$<br>8.39 $O_2$<br>13.64 CO<br>20.18 $H_2O$<br>34.30 $CO_2$ | 325° C. | 1.4 | 24.88 | 93.10 | N.D.* |
| 10 | 12.09 $C_3H_6$ | 350° C. | 1.4 | 47.11 | 99.00 | N.D.* |

TABLE III-continued
RECYCLE EXAMPLES OF THE INVENTION

| Example No. | Feed Compositions in Vol. % | Temp. | Contact Time in Seconds | % Conversion | Acrolein Yield | Acrylic Acid Yield |
|---|---|---|---|---|---|---|
| | 11.13 C$_3$H$_8$ | | | | | |
| | 8.39 O$_2$ | | | | | |
| | 13.64 CO | | | | | |
| | 20.18 H$_2$O | | | | | |
| | 34.30 CO$_2$ | | | | | |
| 11 | 12.09 C$_3$H$_6$ | 325° C. | 1.4 | 33.54 | 97.83 | N.D.* |
| | 11.13 C$_3$H$_8$ | | | | | |
| | 8.39 O$_2$ | | | | | |
| | 13.64 CO | | | | | |
| | 20.18 H$_2$O | | | | | |
| | 34.30 CO$_2$ | | | | | |
| 12 | 12.09 C$_3$H$_6$ | 350° C. | 1.4 | 52.52 | 99.8 | N.D.* |
| | 11.13 C$_3$H$_8$ | | | | | |
| | 8.39 O$_2$ | | | | | |
| | 13.64 CO | | | | | |
| | 20.18 H$_2$O | | | | | |
| | 34.30 CO$_2$ | | | | | |
| 13 | 32.32 CO$_2$ | 350° C. | 1.4 | 80.00 | 90.00 | .07% |
| | 18.22 H$_2$O | | | | | |
| | 11.92 C$_3$H$_6$ | | | | | |
| | 11.07 C$_3$H$_8$ | | | | | |
| | 11.81 O$_2$ | | | | | |
| | 14.39 CO | | | | | |

*N.D. = not detected

EXAMPLE 14

The equipment and procedures of Examples 1 through 8 were employed except a feed was used containing 25.7% by volume of water, 17.93% by volume of propylene, 9.70% by volume of oxygen and the balance nitrogen. Running at a temperature of 375° C. and a contact time of 3.3 seconds the product gas contained 32.6% water, 0.52% CO$_2$, 0.17% acetaldehyde, 1.93% oxygen, 47.77% nitrogen and 6.53% acrolein. This represented a conversion of 31.34% based on the propylene fed and a yield or selectivity to acrolein of 97.32%. No detectable amounts of acrylic or acetic acids were found.

EXAMPLE 15

Using the same feeds and the same conditions as in Example 14 except that the temperature was 350° C. an acrolein yield of 98.55% was achieved at a conversion of 19.02% again based on the propylene fed. The oxygen in the exit gas stream under these conditions was 5.55%. Again no acrylic acid or acetic acid were detected as byproducts.

EXAMPLE 16

The procedure and equipment of Example 1 was repeated except that the temperature was 375° C. and the feed was 29.79 volume percent water, 14.90 volume percent propylene, 9.20 volume percent oxygen with the balance being nitrogen. A yield of 97.3% acrolein was obtained with 2.53% oxygen in the exit gas stream at a conversion of 44.7% based on the propylene fed. No acrylic or acetic acid was detected in the exit gas stream.

The α,β-unsaturated aldehydes of this invention are useful as intermediates in the preparation of various polymers, resins, rubber accelerators, insecticides and tetrahydrofuran. Tetrahydrofuran is useful as a solvent for natural and synthetic resins.

While the invention has been described in considerable detail in the foregoing, it is to be understood that such detail is solely for the purpose of illustration and that variations can be made by those skilled in the art without departing from the spirit and scope of the invention except as set forth in the claims.

I claim:

1. The vapor phase selective oxidation process for the preparation of an α,β-unsaturated aldehyde and less than 2% α,β-unsaturated acids based on the unsaturated aldehyde which comprises contacting a reactant gas containing 1 to 30 volume percent of an olefin of 3 to 5 carbon atoms, from 0 to 40 volume percent of H$_2$O, from 0.25 to 2 times the concentration of olefin but within the range of 2 to 15 volume percent of oxygen and 15 to 97 volume percent of one or more inert gases selected from the group consisting of carbon dioxide, carbon monoxide, nitrogen and hydrogen with a catalyst of the general formula:

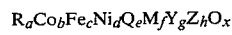

$$R_aCo_bFe_cNi_dQ_eM_fY_gZ_hO_x$$

where
R = Bi or Sb
Q = Mo, W, V or mixtures thereof
M = P, Si or Te
Y = alkali or alkaline earth metals
Z = Ag or Tl and a is 0.6 to 6.0; b is 0 to 3.9; c is 0 to 10.2; d is 0 to 10.2; e is 12; f is 0 to 2.0; g is 0 to 2.0; h is 0 to 0.20 and x is as required to satisfy valence of the other elements with the proviso that Σb+c+d must be >6, and
Σb+d must be >5 for a contact time and at a temperature of from 300° to 500° C. and pressure of from atmosphere to 10 atmospheres to obtain a gaseous product stream comprising an α,β-unsaturated aldehyde at a conversion of from 25 to 80%, a mixture of acids and other aldehydes and a byproduct inert gas or moderator comprising mixtures of gases selected from the group consisting of carbon dioxide, carbon monoxide, water, hydrogen, nitrogen, unreacted olefin with a C$_1$ to C$_4$ saturated hydrocarbon impurity mixture and at least 1% by volume oxygen, separating the byproduct gas from the product stream, recycling said byproduct gas to contact the catalyst together with additional propylene, oxygen and water to achieve the initial gas composition and separating and recovering the α,β-unsaturated aldehyde.

2. The process of claim 1 wherein the conversion is 35 to 70%.

3. The process of claim 1 wherein the conversion is 40 to 70%.

4. The process of claim 1 wherein the oxygen in the reactant gas is 1 to 1.5 times the concentration of the olefin.

5. The process of claim 1 wherein the oxygen in the reactant gas is 1 to 1.3 times the concentration of the olefin.

6. The process of claim 1 wherein the volume percent of H$_2$O is 10 to 40 and the volume percent of inert gas is 25 to 88.

7. The process of claim 1 wherein the inert gas is CO$_2$.

8. The process of claim 1 wherein the inert gas is CO and CO$_2$.

9. The process of claim 1 wherein the byproduct gas is oxygen, hydrogen, unreacted olefin, CO$_2$, CO and a C$_1$ to C$_4$ saturated hydrocarbon impurity mixture.

10. The process of claim 1 wherein the contact time is from 0.1 second to 10 seconds.

11. The process of claim 1 wherein the contact time is from 0.5 second to 4 seconds.

12. The process of claim 1 wherein the reactant gas contains 1 to 15% by volume of olefin.

13. The process of claim 1 wherein the reactant gas contains 5 to 12% by volume of olefin.

14. The process of claim 1 wherein a is 0.7 to 5.0; b is 1.0 to 3.7; c is 1.0 to 4.0; d is 0.5 to 8.0; f is 0.05 to 0.40 and g is 0.05 to 0.20.

15. The process of claim 1 wherein a is 0.8 to 3.6; b is 1.5 to 3.5; c is 1.5 to 3.5; d is 1.0 to 7.0; f is 0.06 to 0.35 and g is 0.06 to 0.15.

16. The process of claim 1 wherein the temperature is from 300° to 400° C.

17. The process of claim 1 wherein the temperature is from 310° to 380° C.

18. The process of claim 1 wherein the pressure is from 1 to 4 atmospheres.

19. The process of claim 1 wherein the pressure is from 1.5 to 3.5 atmospheres.

20. The process of claim 1 wherein R is Bi; Q is Mo; U is P; Y is K; a is 0.9; b is 3.3; c is 2.69; d is 2.0; e is 12; f is 0.24; g is 0.09 and h is 0.

21. The process of claim 1 wherein the $\Sigma + b + C + d$ is between 7 and 11.

22. The process of claim 1 wherein the olefin is propylene and the $\alpha,\beta$-unsaturated aldehyde is acrolein.

23. The process of claim 22 wherein the byproduct gas is a mixture of gases selected from oxygen, hydrogen, $CO_2$, CO, unreacted olefin and essentially propane.

24. The process of claim 22 wherein the inert gas in the reactant gas is $CO_2$.

25. The process of claim 22 wherein the inert gas in the reactant gas is $CO_2$ and CO.

26. The process of claim 22 wherein the conversion is 35 to 70%.

27. The process of claim 22 wherein the oxygen in the reactant gas is 1 to 1.5 times the concentration of the olefin.

28. The process of claim 22 wherein the contact time is from 0.1 to 10 seconds.

29. The process of claim 22 wherein a is 0.7 to 5.0; b is 1.0 to 3.7; c is 1.0 to 4.0; d is 0.5 to 8.0; f is 0.05 to 0.40 and g is 0.05 to 0.20.

30. The process of claim 22 wherein the temperature is 300° to 400° C.

31. The process of claim 22 wherein the pressure is 1 to 4 atmospheres.

32. The process of claim 22 wherein R is Bi; Q is Mo; U is P; Y is K; a is 0.9; b is 3.3; c is 2.69; d is 2.0; e is 12; f is 0.24; g is 0.09 and h is 0.

* * * * *

UNITED STATES PATENT OFFICE
CERTIFICATE OF CORRECTION

PATENT NO. : 4,335,264
DATED : June 15, 1982
INVENTOR(S) : Paul C. Yates

It is certified that error appears in the above-identified patent and that said Letters Patent are hereby corrected as shown below:

In claim 1, column 16, line 45, that portion of the claim reading "together with additional propylene," should read -- together with additional olefin of 3 to 5 carbon atoms --.

Signed and Sealed this

Nineteenth Day of October 1982

[SEAL]

Attest:

GERALD J. MOSSINGHOFF

Attesting Officer

Commissioner of Patents and Trademarks